United States Patent [19]

Chapman

[11] 4,348,329

[45] Sep. 7, 1982

[54] BIOCOMPATIBLE SURFACES

[76] Inventor: Dennis Chapman, Royal Free Hospital School of Medicine, 8, Hunter St., London WC1, England

[21] Appl. No.: 218,556

[22] Filed: Dec. 22, 1980

[30] Foreign Application Priority Data

Dec. 20, 1979 [GB] United Kingdom ............... 7943936
Oct. 15, 1980 [GB] United Kingdom ............... 8033221

[51] Int. Cl.$^3$ ........................... C07F 9/02; A23J 7/00
[52] U.S. Cl. ................................... 260/403; 260/945; 204/159.22; 526/277
[58] Field of Search ........................... 260/403, 945

[56] References Cited

U.S. PATENT DOCUMENTS 3,577,446  5/1971  Rakhit ............................. 260/403
4,229,360 10/1980  Schneider et al. ................ 260/403

OTHER PUBLICATIONS

Biochimica et Biophysica Acta, vol. 602, No. 1, Mar. 1980, pp. 57 to 69.
Chemical Abstracts, vol. 92, No. 9, Jun. 10, 1980, p. 2, Abstract No. 181708e.

*Primary Examiner*—John F. Niebling
*Attorney, Agent, or Firm*—Donald Brown

[57] ABSTRACT

New phospholipids containing a conjugated di-yne system have the formula:

$$\begin{array}{l} CH_2-O-B_1 \\ | \\ CH-O-B_2 \quad O \quad\quad\quad\quad R \\ | \quad\quad\quad\quad \| \quad\quad\quad\quad \oplus / \\ CH_2-(O)_n-P-O-(CH_2)_m-N-R \\ \quad\quad\quad\quad | \quad\quad\quad\quad\quad \backslash \\ \quad\quad\quad\quad O^\ominus \quad\quad\quad\quad\quad R \end{array}$$

wherein at least one of $B_1$ and $B_2$ is a group of the formula $$-(CO)_p-X_1-C\equiv C-C\equiv C-Y_1$$

wherein p is 0 or 1, $X_1$ is a direct bond or a divalent aliphatic or cycloaliphatic group, $Y_1$ is H or a monovalent aliphatic or cycloaliphatic group, the total number of carbon atoms in $X_1$ and $Y_1$ in each of $B_1$ and/or $B_2$ being 8 to 26; and the other of $B_1$ and $B_2$ is either (a) the same or a different group of the formula:

$$-(CO)_p-X_1-C\equiv C-C\equiv C-Y_1$$

where $X_1$, $Y_1$ or p are as defined above;

or (b) is an aliphatic or cycloaliphatic group containing at least 8 carbon atoms; n is 0 or 1, m is 2, 3 or 4 and each R independently represents an alkyl group containing 1 to 4 carbon atoms, and are prepared by esterification and/or etherification of glycerol by conventional techniques. The conjugated di-yne systems can be cross-linked by actinic radiation to give intermolecular and, in certain cases, also intramolecular cross-linking. Thin layers of the phospholipids can be coated onto substrates subsequently to be brought into contact with blood or other body fluids and then cross-linked to give polymer coated surfaces which have a reduced tendency to initiate blood coagulation, for example, compared to untreated surfaces. Artificial lenses for the human eye treated in this way have a reduced tendency to cause endothelial damage. The phospholipids of the invention can also be formed into liposomes and the conjugated di-yne system then cross-linked. Physiologically active materials such as drugs, enzymes or antigens can be incorporated into the liposomes which can then be used as prolonged release formulations.

8 Claims, No Drawings

BIOCOMPATIBLE SURFACES

The invention relates to biocompatible surfaces, that is to say surfaces suited to prolonged contact with living tissues and body fluids and more specifically is directed to new phospholipids, their preparation, to polymers derived therefrom, to the production of the polymers and to the use of the phospholipids and their polymers in the production of biocompatible surfaces and compositions giving prolonged release of physiologically active compounds.

It is common practice to employ biocompatible polymers to form at least the surface of for example prostheses and components of blood dialysis equipment. However, these materials are not perfect and reaction with the living tissues remains a problem; for example surface-induced thrombosis is still a major difficulty, particularly where large quantities of blood are contacted with a foreign surface such as in artificial lungs and kidneys. Formation of a clot in an artificial organ has a number of adverse or even catastrophic effects including occlusion of the blood pathway in the extracorporeal system, or embolism if the clot breaks off the artificial surface and lodges in a host blood vessel. In recent times, surface thrombogenicity has frustrated attempts to use prolonged-maintenance artificial hearts; many of the deaths occurring in animals supported by an artificial heart are caused not by mechanical failure of the heart, but by clot formation. Dialysis membranes, heart valves, circulatory-assist devices, blood substitutes and artificial lungs all share this problem.

It is known that for general biocompatibility the materials used in medical applications should desirably:

(a) be capable of reproducible manufacture as pure materials;
(b) be capable of being prepared without being degraded or adversely changed;
(c) have the requisite mechanical and permeability properties for the specific function;
(d) be sterilizable without adverse changes in mechanical, permeability, or surface properties;
(e) not be acted upon in a detrimental way by the biological environment;
(f) not be carcinogenic.

In applications involving direct contact with blood further restrictions exist. Materials should not:

(i) induce significant thrombosis nor interfere with the normal clotting mechanism;
(ii) cause any significant damage to the cellular elements or soluble components of the blood.

There have been many attempts to prepare biocompatible, and specifically blood compatible, surfaces i.e. those which do not activate the blood coagulation process and do not promote thrombosis formation. Examples of such attempts include the preparation of negatively charged surfaces such as anionic polymers, or suitably oriented electret polymers, surfaces charged with the natural anticoagulant heparin or synthetic heparin analogues, surfaces such as silicone rubber with inherently low surface free energy, albumin-coated surfaces, and surfaces such as some polymethanes which are throught to absorb albumin preferentially from blood. All however have had limitations.

In considering the problem as a general matter of the nature of surfaces it has struck us as significant that biological membranes are important in all areas of the body. Every living cell has an outer membrane, and within the cell there are membranes that act to compartmentalise the various organelles, e.g. the mitochrondria, nucleus, and endoplasmic reticulum. The various cell membranes are built from a matrix of polar lipids (e.g. phospholipids). Thus red blood cells for example have a cell wall constructed on a matrix of a phospholipid bilayer. The lipids are arranged asymmetrically, with the phospholipids lecithin (phosphatidyl choline) and sphingomyelin on the outer surface, and phosphatidylserine and phosphatidylethanolamine on the inner surface, of the wall. The latter have a net negative charge and are known to cause blood coagulation on their own. The former have a zwitterion structure, and form the outer surface of the cell wall.

The invention is based on a realisation that since phospholipids are an essential constituent of biological membranes throughout the body, an imitation of the surface given to these membranes by the phospholipids, on the surface of foreign materials to be in contact with living tissues, might render them biocompatible.

We have found that this is indeed so and the essential of our proposal is to provide an article or body having an artificial biocompatible surface wherein phosphorus oxy-acid/-nitrogen zwitterion groups are present at the external face of the molecular structure.

In its broadest aspect the present invention provides a conjugated di-yne of the general formula:

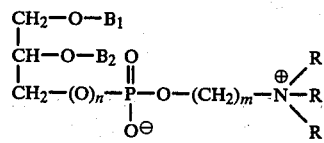

wherein at least one of $B_1$ and $B_2$ is a group of the formula:

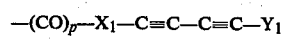

wherein p is 0 or 1, $X_1$ is a direct bond or a divalent aliphatic or cycloaliphatic group, $Y_1$ is H or a monovalent aliphatic or cycloaliphatic group, the total number of carbon atoms in $X_1$ and $Y_1$ in each $B_1$ and/or $B_2$ being 8 to 26, and the other of $B_1$ and $B_2$ is either (a) the same or a different group of the formula:

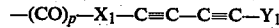

or (b) is an aliphatic or cycloaliphatic group containing at least 8 carbon atoms; n is 0 or 1, m is 2, 3 or 4 and each R independently represents an alkyl group containing 1 to 4 carbon atoms.

A further aspect of the present invention provides a polymer obtained by cross-linking a conjugated di-yne as defined above. These polymers will normally contain repeat units of the structure

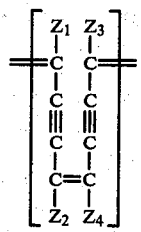

where two of $Z_1$, $Z_2$, $Z_3$ and $Z_4$ represents $Y_1$, as defined above, the other two of $Z_1$, $Z_2$, $Z_3$ and $Z_4$ each represent $-X_1-(CO)_p-G$ where $X_1$ and $p$ are as as defined above and G represents

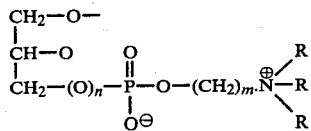

where n, m and R are as defined above, the cross-linked chains being bonded to the same or different G residues.

The conjugated di-ynes of formula I are preferably those in which the zwitterionic group is the phosphate-linked group of the natural phospholipid lecithin and sphingomyelin, namely the choline phosphate group:

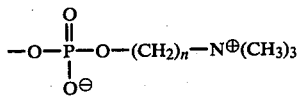

or the related phosphine-linked group:

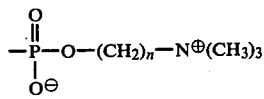

The preferred zwitterionic group is the analogue of the naturally occurring product in which m is 2 but m can also be 3 or 4 and, while it is preferred that each R group is methyl, as it is in the naturally occurring products, R may also be ethyl, propyl or butyl and the zwitterionic group can be unsymmetrically substituted at the quaternary nitrogen.

It is also preferred that in the conjugated di-ynes of the invention, both $B_1$ and $B_2$ each represent a group of the formula:

As a practical matter, symmetrical compounds are the easiest to synthesise, that is to say compounds in which, in $B_1$ and $B_2$, p, $X_1$ and $Y_1$ are identical. Such symmetry, however, is not essential, in accordance with the present invention and it is possible to utilise compounds in which in one of $B_1$ and $B_2$ p is zero and in the other of $B_1$ and $B_2$ p is 1 where each $X_1$ and $Y_1$ are identical or different. However, it is more difficult to synthesise such materials.

So far as the theoretical basis of this invention is concerned, the position of the conjugated di-yne system in the $B_1$ and $B_2$ residue is not critical. For example, $X_1$ can be a direct bond so that the conjugated di-yne is immediately adjacent to the carboxylic ester or ether and in such a case $Y_1$ would need to contain at least 8 carbon atoms. It is also equally possible for the conjugated di-yne system to be at that end of the hydrophobic chain remote from the carboxylic ester or ether function so that $Y_1$ is hydrogen and $X_1$ contains at least 8 carbon atoms. However, for reasons which will be discussed in more detail below, we usually find it most convenient to arrange for the conjugated di-yne system to be located towards the centre of the hydrophobic chain so that there is approximately the same number of carbon atoms in $X_1$ and $Y_1$.

$X_1$ and $Y_1$ are each preferably an aliphatic or cycloaliphatic group. Although our initial experiments have concentrated upon compounds in which the aliphatic or cycloaliphatic groups were unbranched hydrocarbon groups, in principle, there is no reason why the aliphatic or cycloaliphatic groups should not be branched-chain hydrocarbon groups or should contain substituents on the hydrocarbon chains, for example alkoxy substituents or halogen. For reasons which will become apparent in the discussion below, we prefer that the conjugated di-yne system represents the only carbon to carbon unsaturation in the hydrophobic chain but if additional cross-linking is desired, further carbon to carbon unsaturation could occur in the groups $X_1$ and $Y_1$.

It is important that the total number of carbon atoms in $X_1$ and $Y_1$ in each group $B_1$ and $B_2$ be 8 to 26 carbon atoms so that each hydrophobic chain contains a total of 12 to 30 carbon atoms. We have found that if the group $B_1$ and/or $B_2$ contains less than 12 carbon atoms, the resulting material is difficult to polymerise except at very low temperatures. As a practical matter, we find that the most satisfactory results are obtained when there is between 16 and 26 carbon atoms in the groups $B_1$ and/or $B_2$ and particularly when the chain contains 22 or 24 carbon atoms.

While the exact structural configuration of the carbon atoms in $X_1$ and $Y_1$ are not critical to the present invention, their main functions being to impart the correct degree of hydrophobicity to the compounds and to permit polymerisation at a convenient temperature, it is not essential that the carbon atoms be in a straight chain or branched configuration but the groups $X_1$ and $Y_1$ can also include cycloaliphatic residues containing 3 to 8 or even more carbon atoms in a cycloaliphatic configuration.

For reasons which will become apparent from the discussion below concerning polymerization of the conjugated di-ynes, it is preferred that both $B_1$ and $B_2$ include the conjugated di-yne system so that the conjugated di-yne system can participate in both intramolecular and intermolecular polymerisation. However, a sufficient degree of cross-linking can be obtained simply by intermolecular polymerisation in which case it is only essential that one of the groups $B_1$ and $B_2$ contain the conjugated di-yne system. When only one of $B_1$ and $B_2$ contains the conjugated di-yne system, the other of $B_1$ and $B_2$ may be an aliphatic or cycloaliphatic residue, preferably hydrocarbon residue, which can be saturated or may contain olefinic or perhaps single acetylenic unsaturation which can be isolated or in conjugation with the conjugated di-yne system. Such groups are again bonded to the glycerol residue through an ester or ether group and should again contain at least 12 carbon atoms.

The conjugated di-ynes of the invention may be prepared by procedures known per se. Thus, the zwitterionic group can be introduced by subjecting the appropriate phosphonic or phosphinic acid or an esterifiable derivative thereof to reaction with glycerol or an esterifiable derivative thereof whereby the α-hydroxy group of glycerol reacts to form the necessary phosphorus ester group. The groups $B_1$ and $B_2$ can be introduced into the molecule by esterification or etherification using a carboxylic acid $B_1COOH$ or an alcohol $B_1OH$ or the corresponding $B_2COOH$ or BOH material, or an ester- or ether-forming derivative of one of these carboxylic acids or alcohols with glycerol or an ether-forming or ester-forming derivative thereof. These reactions can be carried out between the glycerol or derivative thereof on the one hand and the carboxylic acid or alcohol and the phosphorus ester on the other hand either simultaneously or subsequently in either order. For the production of symmetrical phospholipids, which are the preferred compounds of the invention, we find it convenient, in practice, first to form the required glycerol monoester with the selected phosphorus or phosphoric acid and then to react this monophosphorus ester with the anhydride of the selected conjugated di-yne carboxylic acid (obtained by treating the acid with dicyclohexyl-carbodiimide) and then reacting the glycerol monoester with the anhydride in an organic solvent and in the presence of an organic base.

Other known methods for the formation of ester groups can equally well be used. When it is desired to produce a compound in which p is 0, then corresponding conventional ether-forming processes can be used.

The conjugated di-ynes of the invention can be polymerised by subjecting them to actinic radiation, normally ultra-violet radiation of wavelengths in the range <300 nm. Such irradiation produces a cross-linking between the conjugated di-yne systems in adjacent chains. This gives rise to a polymer containing repeat units of the structure:

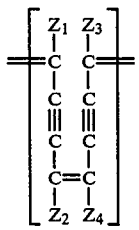

wherein $Z_1$, $Z_2$, $Z_3$ and $Z_4$ are as defined above. The conjugated di-yne system involved in the cross-linking is an unsymmetrically substituted di-yne. Cross-linking involves $C_1$ and $C_4$ of the 4 carbon atom chain of the conjugated di-yne but since $C_1$ and $C_4$ are not equivalent to each other, because of the unsymmetrical substitution, various cross-linked products can be produced depending upon whether cross-linking occurs between $C_1$ and $C_1$ in each chain or between $C_1$ and $C_4$ or between $C_4$ and $C_4$. For example, if cross-linking occurs between $C_1$ and $C_4$, the repeat unit will be

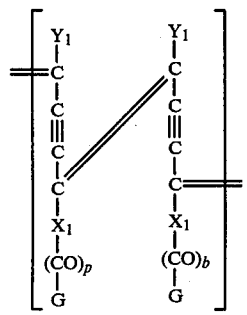

Our structural studies on the polymers have no yet established whether or not cross-linked polymers contain one or more than one of the possible cross-linked products but they have established that they contain the conjugated system

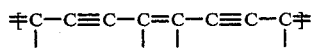

which is common to all the cross-linked structures.

When both $B_1$ and $B_2$ contain conjugated di-yne systems, there will be both intramolecular and intermolecular cross-linking which is desirable for most applications of the polymers of this invention. For this reason, it is preferred that both $B_1$ and $B_2$ contain the conjugated di-yne system and, in order to optimise the intramolecular cross-linking, it is preferred that the relative positions of the conjugated di-yne system in Band $B_2$ be approximately the same, in other words, that the carbon chains connecting the conjugated di-yne systems to the glycerol residue should not differ in length by more than 2 carbon atoms.

In view of the intended biomedical application of the polymers of this invention, polymerisation is normally best induced by exposure to actinic radiation, normally that having a wavelength shorter than that of visible light but in principle, any method to be capable of inducing polymerisation of conjugated di-yne systems can be used for the production of the polymers of this invention. The conjugated di-yne can be polymerised in various states, for example as monolayers on water, as multi-layers on a hydrophobic substrate e.g. Teflon, as liposomes or in a solid state in a KBr disc.

One of the major uses of the polymers of this invention is to provide surface coatings onto substrates, particularly those substrates which are to be brought subsequently into direct contact with blood or another body fluid or an internal body surface. Such surface coatings are, in practice, normally best introduced by coating the substrate with the conjugated di-yne of the invention and then polymerising the conjugated di-yne in situ by exposure to actinic radiation. The conjugated di-ynes of the invention are colourless materials but as polymerisation proceeds, there is a noticeable colour change proceeding first through the blue range when the conjugated di-yne is converted first to an intermediate carbene, and this transitory carbene intermediate is then transformed into the final polymer molecule which has a red or purple coloration. Consequently, polymerisation on the substrate can be followed visually. The substrates may for example be polymers, metals, glass, ceramics and many others, examples of polymers being cellophane, polyvinyl chloride, polycarbonate, polymethylmethacrylate polyethylene, polytetrafluoroethylene and silicon rubber. Such coated substrates may be used in prosthetic implants, eye implants and contact lenses, diagnostic devices, lung machines, kidney machines, suture threads, artificial lenses, disposable tissues, culture vessels and other surgical instruments, gloves, catheters, permanent entry ports, drug delivery systems, apparatus and vessels used for the study of blood, syringes, contraceptive devices including intra uterine appliances, and wound dressings.

The present invention is particularly suitable for providing a surface coating on intraocular lenses to reduce corneal endothelial damage.

Primary implantation of an intraocular lens can significantly increase the endothelial cell loss and damage associated with cataract extraction. This damage appears to be caused by instantaneous adherence of the lens material, polymethylmethacrylate (PMMA), to the endothelial surface if the lens touches the corneal endothelium.

Using electron microscopy, Kaufman and Katz demonstrated that even momentary contact between the lens, made of PMMA and corneal endothelial cells resulted in tearing of the cell membranes from adherence to the IOL surface.

Research on surface modifications of polymethylmethacrylate which would reduce or prevent such cell damage in the event of occasional lens-endothelial contact appears to be a practical approach, since this polymer has already been shown to be well tolerated intraocularly without exhibiting significant short or long-term degradation. The alternative of introducing a new material would require reptition of similarly extensive safety and efficacy tests.

Previous work in this area has been based on the idea that the adherence between the lens and endothelium is an interaction between the hydrophobic polymethylmethacrylate and the hydrophilic intraocular tissues. Rendering the polymethylmethacrylate surface hydrophilic by dipping it in polyvinyl pyrrolidone (PVP) or methylcellulose solutions prior to implantation has been shown to reduce clinical incidence of endothelial damage. Similar attempts to temporarily alter these intraocular lens surfaces have employed dipping solutions of PVP, silicone oil and blood serum. However, dipping these lenses into a solution immediately before surgery can be both messy and inconvenient, and also introduces new problems of sterility and reproducibility.

The materials of the present invention are used to coat the intraocular lens so that their polar groups of the invention materials face the extracellular fluids. The surface coatings on the lens is therefore similar to that of a cell membrane surface. This makes it suitable for short or prolonged contact with living tissues and body fluids and should reduce tearing of endothelial cell membranes. The conjugated di-ynes are then stabilised to form a polymeric coating whose surface is hydrophilic and which is at the same time biocompatible to the living tissue.

Intraocular lenses or other substrate surfaces can be coated by a variety of techniques for example solution or emulsion coating or Langmuir-Blodgett multilayer dipping techniques, giving oriented layers and enabling irregular surfaces to be treated.

Attachment of the coating may be improved by covalent bonding to the surface, for example using lipids having groups, within or terminating the chains of the fatty acids, that are reactive with the material of the polymer or other surface to be coated or with a material absorbed by it, e.g. after solvent treatment. Alternatively there may be physical attachment of the coating, for example by swelling a polymer substrate by means of a low molecular weight solvent with subsequent absorption, into the polymer structure, of the lipid chains of the fatty acid residues.

Another important application of the conjugated di-ynes of the present invention is in the production of liposomes as such liposomes can be used to carry physiologically active materials and so provide a biocompatible formulation which will give a sustained release of, for example, a non-metabolisable drug or enzyme to the body.

Such liposomes can be prepared by dispersion of the conjugated di-yne in an aqueous medium, raising the temperature of the dispersion to one above the lipid or Chapman transition temperature which is the temperature at which liposome formation occurs and then cooling the dispersion back to ambient temperature. If a physiologically active material is present in the aqueous medium during liposome formation, the liposomes will contain the active material and slowly release the active material over a prolonged period as a result of metabolism of the liposome membrane structure. One of the practical advantages of such an arrangement is that it is possible to formulate in this way both water-soluble and water-insoluble active materials or, if desired, to formulate both water-soluble and water-insoluble materials in the same formulation, the water-insoluble material being first incorporated in the lipid.

It is often found that the conjugated di-yne phospholipid of the invention or their polymers which form the membranes of the liposomes, will act as adjuvants of many physiologically active materials incorporated in the liposomes.

It is also possible to incorporate aluminium hydroxide or other adjuvants in these formulations to potentiate the activity of the physiologically active material by introducing aluminium hydroxide or other adjuvants into the aqueous medium during liposome formation.

Liposome formation can be carried out by known techniques to product multi-lamellar liposomes. Small diameter unilamellar liposomes can be generated by subjecting the multi-lamellar liposomes to ultrasonic vibration. Larger unilamellar liposomes can be generated by dissolving the conjugated di-yne in alcohol and then injecting this solution e.g. through a syringe, into an aqueous medium. These unilamellar materials are sometimes known as microvesicles.

The resulting liposomes, either unilamellar or multilamellar, and normally also incorporating a physiologically active material and perhaps an adjuvent can be stabilised by cross-linking the conjugated di-yne system by exposure to actinic radiation as described above. Such irradiation will bring about intermolecular, and, depending upon the structure of the conjugated di-yne, perhaps also intramolecular cross-linking to give a liposome dispersion comprising polymers of the present invention. It is also possible to include liposomes of other phospholipids in the liposome dispersion of the present invention prior to or subsequently to the cross-linking of the conjugated di-ynes of this invention.

While it is normally most convenient to formulate the polymers of the present invention in liposome form, it is also possible to polymerise the conjugated di-ynes in bulk and then to extrude the polymer to give a phospholipid polymer capsule. Alternatively, the phospholipid polymer of the invention can be included in liposome systems based on other phospholipids.

A wide variety of physiologically active materials can be formulated in the liposome dispersions of the invention including antigenic material, hormones, enzymes and drugs such as anti-inflammatory agents. The formulation of influenza virus or fragments thereof, diphtheria toxin, tetanus toxin and other antigenic material derived from viral or bacterial sources in liposomes is now well documented in the literature as is the formulation of hormones such as insulin, anti-inflammatory steroids such as corticosteroids e.g., cortisone, cortisol and their $\Delta'$-dehydro- and 9-fluoro derivatives; anti-inflammatory non-steroids, e.g. peptides; immunosuppresive compounds such as methotrexate; salicylates; phenyl butazone; and inhibitors for hydrolytic enzymes. For further discussion as to how these and other physiologically active materials may be incorporated into liposome compositions reference may be made for example to U.S. Pat. Nos. 4,177,113 and 4,199,565 and to German Offenlegungsschriften 22 49 522, 25 48 411, 26 43 641, 27 12 030 and 27 12 031. These materials are typical of the physiologically active materials that may be incorporated into the liposomes of the present invention.

The following Examples are given to illustrate the invention.

EXAMPLE 1

Production of conjugated di-yne phospholipids (a) Synthesis of diacetylenic acids A schematic outline of the synthesis is shown below:

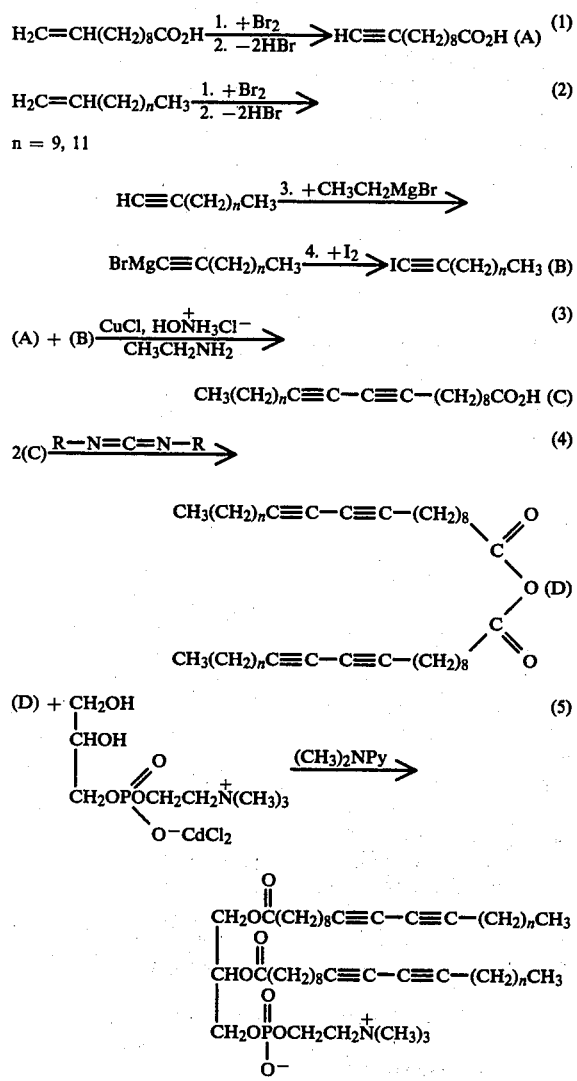

The alkenes and alkenoic acid were brominated in petroleum ether by slowing adding 1 mol-equiv. of bromine. The dibromo derivatives were immediately dehydrobrominated by refluxing them in ethanol with excess KOH. After the alcohol had been distilled off and dilute HCl added, alkyne was isolated by ether extraction and purified by vacuum distillation ($10^{-3}$ mmHg).

For an asymmetrical Chodkiewicz coupling, one of the reactants had to be iodinated. The 1-alkynes were therefore added to a slight excess of ethylmagnesium bromide in dry diethyl ether ($CaH_2$-treated). The acetylenic Grignard reagent formed reacts directly with added $I_2$ to give the halo derivative desired. The contents of the reaction flask were poured into excess dilute acetic acid and the iodoacetylene extracted into diethyl ether. Unreacted $I_2$ was removed by a thiosulphate wash and after the diethyl ether had been evaporated purification was achieved by vacuum distillation.

The details of acetylenic-coupling reactions have been extensively reviewed. To the acid dissolved in dilute KOH solution was added a trace of hydroxylamine hydrochloride and 0.25 mol-equiv. of $Cu_2Cl_2$ dissolved in aqueous ethylamine. The iodoalkyne (1 mol-equiv.) was then added, a small portion at a time. The originally yellow solution turned green. The yellow colour was restored by adding a few drops of 10% hydroxylamine solution before the next addition of alkyne. Finally, the reaction mixture was acidified and the product extracted into diethyl ether. The diynoic acid was recrystallized from 40°–60° C. petroleum ether.

The acids readily polymerised. Ultraviolet and infrared spectroscopy showed the presence of conjugated triple bonds and a carboxylic acid group, respectively.

(b) Synthesis of phospholipids

The acid was dissolved in methylene chloride and converted to the anhydride by adding 0.55 mol.-equiv. of dicyclohexylcarbodiimide. The anhydrides were characterised by infrared spectroscopy.

Phospholipids were synthesized by using the method of Gupta et al. Glycerophosphatidylcholine-$CdCl_2$ complex (1.0 mol-equiv.) was stirred with anhydride (2.5 mol-equiv.) and 4-N,N-dimethylaminopyridine (2.0 mol-equiv.) in dry chloroform ($P_2O_5$-treated) for 30 h. After removal of the solvent, the methanol/chloroform/water (5:4:1, v/v) soluble fraction was passed down a column of Rexyn I-300 resin. The product now free of $CdCl_2$ and amino-pyridine was purified by chromatography on Sephadex LH-20. The overall yield based on the starting alkene is 5%.

The product and dipalmitoyl phosphatidylcholine (puriss grade, Fluka) were compared by thin-layer chromatography (Merck silica gel plates; solvent, chloroform/methanol/water (65:35:4, v/v) and infrared spectroscopy. $R_f$ values and spectra were identical. The product gave a positive test (turned blue) when sprayed with Dittmer reagent. Examination by ultraviolet spectroscopy showed that conjugated triple bonds were present. The products are the phospholipids 1,2-ditricosanoyl ($C_{23}$)- and 1,2-dipentacosanoyl ($C_{25}$)-10,12-diyne-sn-glycero-3-phosphorylcholine.

The transition temperatures and enthalpies for these diacetylenic phospholipids ($C_{23}$ and $C_{25}$) are shown below:

| | Diacetylenic phospholipids | | | | | |
|---|---|---|---|---|---|---|
| | $C_{23}$ | $C_{25}$ | DML | DPL | DSL | DBL |
| Number of methylene units | 17 | 19 | 12 | 14 | 16 | 20 |
| Transition temperature (°C.) | 38.5 | 48 | 23 | 41 | 58 | 75 |
| Transition enthalpy | | | | | | |

| -continued | | | | | | |
|---|---|---|---|---|---|---|
| | Diacetylenic phospholipids | | | | | |
| | $C_{23}$ | $C_{25}$ | DML | DPL | DSL | DBL |
| (kcals . mol$^{-1}$) | 10.15 | 13.18 | 6.65 | 8.65 | 10.70 | 14.9 |

"TRANSITION TEMPERATURES AND ENTHALPIES FOR DIACETYLENIC PHOSPHOLIPIDS AND THE FOUR SATURATED PHOSPHATIDYLCHOLINES, $C_{23}$ DIACETYLENIC, $C_{25}$ DIACETYLENIC, DIMRISTOYL (DML), DIPALMITOYL (DPL), DISTEAROYL (DSL) AND DIBEHENOYL (DBL) PHOSPHATIDYLCHOLINES"

EXAMPLE 2

The procedure used in Example 1 was modified to produce the conjugated tri-yne analogue of the $C_{23}$ phospholipid. The alkynoid carboxylic acid HC≡C—(CH$_2$)$_8$COOH was prepared as described in Example 1, step 1. Bis-(chloromethyl)-acetylene was reacted with 3 moles of butyl-lithium in tetrahydrofuran and hexamethyl phosphoramide to give the lithium salt of the diacetylene HC≡C—C≡C$^\ominus$Li$^\oplus$ which is then reacted with n-octyl bromide to form dodecadi-yne-1,3 in about 40% yield. The dodecadi-yne-1,3 is then reacted with NaOI to give the 1-iodo derivative CH$_3$—(CH$_2$)$_7$—C≡C—C≡C—I which was then reacted with alkynoic acid mentioned above under the conditions given in Example 1 step 3 to give the conjugated tri-yne

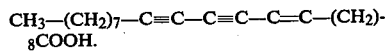
CH$_3$—(CH$_2$)$_7$—C≡C—C≡C—C≡C—(CH$_2$)$_8$COOH.

This conjugated tri-acetylenic acid shows a higher peak in its UV spectrum than the conjugated di-acetylenic acid obtained in step 3 of Example 1, indicating its higher degree of conjugation. The conjugated tri-acetylenic acid was converted to its anhydride by the procedure described in step 4 of Example 1 and the anhydride then reacted with the CdCl$_2$ complex of glycerophosphatidylcholine wa described in step 5 of Example 1 to form the conjugated tri-acetylenic phospholipid which polymerises on exposure to actinic radiation.

The conjugated tri-acetylenic phospholipid was also prepared by reacting the tri-acetylenic carboxylic acid with the ketone

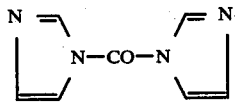

in tetrahydrofuran to form an amide

and this amide then reacted with the CdCl$_2$ complex of the phospholipid in dimethylsulphoxide to give the conjugated tri-acetylenic phospholipid.

The conjugated tri-acetylenic acid was also prepared by a process in which the acid HC≡C.(CH$_2$)$_8$COOH is iodated at the acetylenic bond and the iodo-decynoic acid reacted with the di-yne CH$_3$.(CH$_2$)$_7$—C≡C—C≡CH by the coupling procedure described above.

EXAMPLE 3

The diacetylenic phospholipids of Example 1 were used to coat an intraocular lens made of polymethyl methacrylate using the Langmuir-Blodgett technique. In this technique, a surface layer of the lipid is formed at an air-water interface. A final lipid layer possessing a hydrophilic polar surface is required.

The phospholipid monolayers are spread on CdCl$_2$ containing pure water (1 g/l. CdCl$_2$, resistivity of the water 15 MΩ/cm no detectable organic contaminations). The lens are cleaned by soaking for two hours in a detergent solution (RBS 35) at ~60° C., then thoroughly rinsed in pure water. The monolayers are transferred by repeatedly dipping through the monolayer downward at a comparatively high speed (falling free or ~73 cm/min). Deposition occurs only during upward movement. It is important that, when the coated object is withdrawn into the air, it is withdrawn at a rate of 0.3 cm/min or less so that the final layer will possess an outer hydrophilic surface. The coated lens was then irradiated for 10 seconds at room temperature with an ultra-violet lamp having peak radiation intensity at 254 nm at energy output of 1200 μω/cm$^2$ 15.2 cm from its face. Alternatively, to produce the desired hydrophilic polar surface as the final outer surface, polymerisation by irradiation of the lipid layer whilst the coating (of desired number of monolayers) can be carried out under water and the lens withdrawn after the water surface has been cleaned thoroughly.

The surface pressure of the lipid layers is chosen to be 35 dynes/cm., close to the breakdown pressure of these layers and the temperature was 20–22 Centigrade (room temperature). To minimise the influence of impurities it is necessary to add CdCl$_2$ to the subphase (1g/liter) and to use only freshly spread monolayers. The water is purified by a Millipore water purification system and used immediately after preparation to minimise recontamination.

The hydrophilicity of each surface is assayed by measuring the "water contact angle," defined as the degree of surface spreading of a drop of water. Water forms beads on the surface of standard (hydrophobic) PMMA; however, on the coated surface it spreads for about 10 seconds and rolls off very slowly. This behaviour does not change when the coated perspex is stored on air after several weeks or immersed in water for days. The stability can be seen from the fact that sterilisation processes involving immersion in 70% NaOH solutions for several days does not change the surface properties.

Permanent grafting of the lipid polymers on to intraocular lenses using gamma irradiation results in successful hydrophilic modifications of the lens surface. The water contact angle for unmodified PMMA is 72°; after grafting, this angle decreases (i.e. spreading increased).

These lenses have been subjected to clinical testing. The coated lenses were introduced into human patients without causing endothelial damage and without causing any adverse effects to the patients over a two month test period.

EXAMPLE 4

The coating procedure described in Example 3 was repeated but replacing the lens by flexible Teflon sheets 0.1 mm thick. The coated sheet was polymerised in air as described in Example 3. The flexible sheet was then formed into a tube and blood introduced into the tube. An in vitro fibrinopeptide A generation test was used as a measure of the capacity of the surface to trigger thrombin activity. The surface showed little tendency to initiate blood clotting and was superior in this respect to the untreated Teflon material.

EXAMPLE 5

The coating procedure of Example 3 was repeated but replacing the lens by a silicone contact lens, a glass sheet and a cellulose acetate dialysing membrane (Cuprophane). Visual examination after irradiation showed formation of a polymer film on each of these three substrates. Contact angle measurements on the coated substrates showed that in each case a hydrophilic outer surface had been formed.

EXAMPLE 6

The di-$C_{23}$- di-conjugated phospholipid of Example 1 was introduced into water at 50° C. This is a temperature above its liposome formation temperature and the dispersion was then cooled to ambient temperature when electronmicroscopy showed the presence of multi-lamellar liposomes. This dispersion was then irradiated with ultra-violet light when a colour change was seen in the dispersion indicating polymerisation by cross-linking of the conjugated di-yne system. Spectral changes that were also identified were consistent with an increased conjugated path in the organic materials.

This procedure was repeated introducing the conjugated phospholipid into an aqueous medium containing enzymatically active intrinsic protein $Ca^{2+}$ ATP-ase. Subsequent examination of the resulting liposomes showed that the liposomes exhibited enzymatic activity showing that some enzyme was incorporated in the liposomes.

The procedure described above was repeated using the di-$C_{25}$ conjugated phospholipid of Example 1 but the temperature of the aqueous medium into which it was introduced was raised to 60° C. in order to be above the liposome formation temperature of the di-$C_{25}$ material. Again, it was found that enzymatic activity was detected in the liposomes.

I claim:

1. A conjugated di-yne of the general formula:

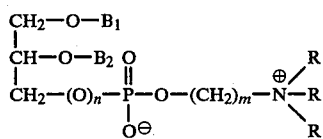

wherein at least one of $B_1$ and $B_2$ is a group of the formula

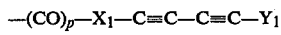

wherein p is 0 or 1, $X_1$ is a direct bond or a divalent aliphatic or cycloaliphatic group, $Y_1$ is H or a monovalent aliphatic or cycloaliphatic group, the total number of carbon atoms in $X_1$ and $Y_1$ in each of $B_1$ and/or $B_2$ being 8 to 26; and the other of $B_1$ and $B_2$ is either (a) the same or a different group of the formula:

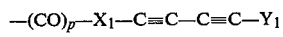

where $X_1$, $Y_1$ or p are as defined above; or (b) is an aliphatic or cycloaliphatic group containing at least 8 carbon atoms; n is 0 to 1, m is 2, 3 or 4 and each R independently represents an alkyl group containing 1 to 4 carbon atoms.

2. A di-yne according to claim 1 wherein $B_1$ and $B_2$ are identical or different groups of the formula:

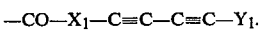

3. A di-yne according to claim 1 or 2 wherein $X_1$ and $Y_1$ are both saturated unbranched hydrocarbon chains, each pair of $X_1$ and $Y_1$ groups containing 10 to 16 carbon atoms.

4. A di-yne according to claim 2 wherein the number of carbon atoms in each $X_1$ is such that the di-yne will undergo both intramolecular and intermolecular cross-linking on exposure to actinic radiation.

5. A di-yne according to claims 1 or 2 wherein n is 1, m is 2 and each R is methyl.

6. A di-yne of the formula:

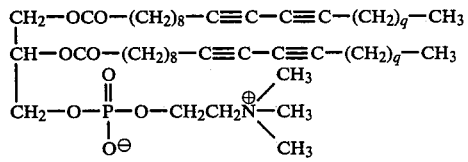

wherein q is 9 to 11.

7. A di-yne of the formula:

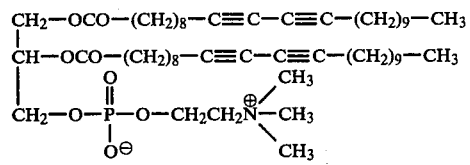

8. A di-yne of the formula:

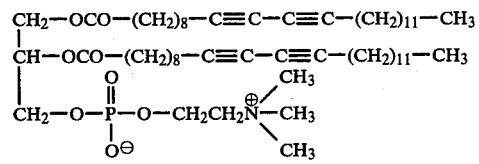

* * * * *